United States Patent
Garabedian et al.

(10) Patent No.: US 7,937,160 B2
(45) Date of Patent: May 3, 2011

(54) METHODS FOR DELIVERING CORTICAL ELECTRODE LEADS INTO PATIENT'S HEAD

(75) Inventors: Robert J. Garabedian, Mountain View, CA (US); Michael P. Wallace, Fremont, CA (US); Gary Heit, Menlo Park, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 219 days.

(21) Appl. No.: 11/010,232

(22) Filed: Dec. 10, 2004

(65) Prior Publication Data

US 2006/0129203 A1 Jun. 15, 2006

(51) Int. Cl.
*A61N 1/05* (2006.01)

(52) U.S. Cl. .......... 607/116; 600/378; 607/45; 606/129; 606/130

(58) Field of Classification Search .................. 607/116, 607/45; 606/129–130; 600/378
See application file for complete search history.

(56) References Cited

U.S. PATENT DOCUMENTS

| | | | |
|---|---|---|---|
| 538,514 A | 4/1895 | Haeseler |
| 661,047 A | 11/1900 | Graves |
| 4,141,365 A | 2/1979 | Fischell et al. |
| 4,285,347 A | 8/1981 | Hess |
| 4,519,403 A | 5/1985 | Dickhudt |
| 4,608,985 A | 9/1986 | Crish et al. |
| 4,658,835 A | 4/1987 | Pohndorf |
| 4,739,768 A | 4/1988 | Engelson |
| 4,813,934 A | 3/1989 | Engelson et al. |
| 4,869,255 A | 9/1989 | Putz |
| 4,884,579 A | 12/1989 | Engelson |
| 5,005,587 A | 4/1991 | Scott |

(Continued)

FOREIGN PATENT DOCUMENTS

EP 0 861 676 9/1998

(Continued)

OTHER PUBLICATIONS

Canavero, Sergio et al., "Extradular Motor Cortex Stimulation for Advanced Parkinson Disease," J. Neurosurg. 97: pp. 1208-1211, 2002.

(Continued)

*Primary Examiner* — Niketa I Patel
*Assistant Examiner* — Joseph Stoklosa
(74) *Attorney, Agent, or Firm* — Vista IP Law Group LLP

(57) ABSTRACT

Methods and kits for delivering an electrode lead into the head of a patient are provided. A burr hole is formed within the cranium of the patient, and an electrode lead is threaded through the burr hole. The electrode lead is then placed in a pre-shaped two-dimensional geometry between the cranium and cortical brain tissue of the patient. An access anchor may be mounted into the burr hole to facilitate introduction and removal of the electrode lead and other devices. In some circumstances, it may be desirable to separate the dura mater overlying the cortical brain tissue from the cortical brain tissue to create a pocket in which the electrode lead may be manipulated. In this case, a tissue layer dissection device can be introduced through the burr hole, operated to separate the dura mater from the cranium, and then removed from the burr hole. In one embodiment, the dissection device comprises a balloon that can be inflated to separate the dura mater and cranium, and then deflated prior to removing the dissection device from the burr hole.

21 Claims, 13 Drawing Sheets

U.S. PATENT DOCUMENTS

| | | | |
|---|---|---|---|
| 5,010,894 A | 4/1991 | Edhag | |
| 5,010,895 A | 4/1991 | Maurer et al. | |
| 5,107,856 A | 4/1992 | Kristiansen et al. | |
| 5,170,802 A | 12/1992 | Mehra | |
| 5,224,491 A | 7/1993 | Mehra | |
| 5,234,437 A | 8/1993 | Sepetka | |
| 5,239,999 A | 8/1993 | Imran | |
| 5,250,071 A | 10/1993 | Palermo | |
| 5,261,916 A | 11/1993 | Engelson | |
| 5,263,488 A | 11/1993 | Van Veen et al. | |
| 5,304,195 A | 4/1994 | Twyford, Jr. et al. | |
| 5,306,272 A * | 4/1994 | Cohen et al. | 606/1 |
| 5,312,415 A | 5/1994 | Palermo | |
| 5,342,410 A | 8/1994 | Braverman | |
| 5,350,397 A | 9/1994 | Palermo et al. | |
| 5,358,514 A | 10/1994 | Schulman et al. | |
| 5,365,926 A | 11/1994 | Desai | |
| 5,374,285 A | 12/1994 | Vaiani et al. | |
| 5,391,200 A | 2/1995 | KenKnight et al. | |
| 5,397,341 A | 3/1995 | Hirschberg et al. | |
| 5,411,551 A | 5/1995 | Winston et al. | |
| 5,417,719 A | 5/1995 | Hull et al. | |
| 5,423,864 A | 6/1995 | Ljungstroem | |
| 5,423,877 A | 6/1995 | Mackey | |
| 5,443,492 A | 8/1995 | Stokes et al. | |
| 5,462,545 A * | 10/1995 | Wang et al. | 606/41 |
| 5,464,446 A * | 11/1995 | Dreessen et al. | 607/116 |
| 5,501,703 A | 3/1996 | Holsheimer et al. | |
| 5,509,411 A | 4/1996 | Littmann et al. | |
| 5,531,779 A | 7/1996 | Dahl et al. | |
| 5,534,007 A | 7/1996 | St. Germain et al. | |
| 5,543,864 A | 8/1996 | Hirschman et al. | |
| 5,582,609 A | 12/1996 | Swanson et al. | |
| 5,603,731 A | 2/1997 | Whitney | |
| 5,611,345 A | 3/1997 | Hibbeln | |
| 5,647,870 A | 7/1997 | Kordis et al. | |
| 5,683,422 A | 11/1997 | Rise | |
| 5,702,438 A | 12/1997 | Avitall | |
| 5,707,354 A | 1/1998 | Salmon et al. | |
| 5,713,922 A | 2/1998 | King | |
| 5,716,377 A | 2/1998 | Rise et al. | |
| 5,752,979 A | 5/1998 | Benabid | |
| 5,755,750 A | 5/1998 | Petruska et al. | |
| 5,782,239 A | 7/1998 | Webster, Jr. | |
| 5,782,798 A | 7/1998 | Rise | |
| 5,792,187 A | 8/1998 | Adams | |
| 5,800,474 A | 9/1998 | Benabid et al. | |
| 5,814,062 A | 9/1998 | Sepetka et al. | |
| 5,833,709 A | 11/1998 | Rise et al. | |
| 5,846,238 A | 12/1998 | Jackson et al. | |
| 5,860,974 A | 1/1999 | Abele | |
| 5,871,483 A | 2/1999 | Jackson et al. | |
| 5,891,136 A | 4/1999 | McGee et al. | |
| 5,902,236 A * | 5/1999 | Iversen | 623/23.65 |
| 5,902,331 A | 5/1999 | Bonner et al. | |
| 5,908,385 A | 6/1999 | Chechelski et al. | |
| 5,925,070 A | 7/1999 | King et al. | |
| 5,928,278 A | 7/1999 | Kitschmann | |
| 5,931,862 A | 8/1999 | Carson | |
| 5,938,689 A | 8/1999 | Fischell et al. | |
| 5,954,761 A | 9/1999 | Machek et al. | |
| 5,967,986 A | 10/1999 | Cimochowski et al. | |
| 5,984,909 A | 11/1999 | Lurie et al. | |
| 6,002,964 A | 12/1999 | Feler et al. | |
| 6,006,124 A * | 12/1999 | Fischell et al. | 600/378 |
| 6,006,134 A | 12/1999 | Hill et al. | |
| 6,015,387 A | 1/2000 | Schwartz et al. | |
| 6,016,449 A | 1/2000 | Fischell et al. | |
| 6,018,682 A | 1/2000 | Rise | |
| 6,027,456 A | 2/2000 | Feler et al. | |
| 6,036,689 A | 3/2000 | Tu et al. | |
| 6,053,873 A | 4/2000 | Govari et al. | |
| 6,066,163 A | 5/2000 | John | |
| 6,074,407 A | 6/2000 | Levine et al. | |
| 6,074,507 A | 6/2000 | Sukenik | |
| 6,091,980 A | 7/2000 | Squire et al. | |
| 6,094,596 A | 7/2000 | Morgan | |
| 6,119,044 A | 9/2000 | Kuzma | |
| 6,122,548 A | 9/2000 | Starkebaum et al. | |
| 6,128,537 A | 10/2000 | Rise | |
| 6,128,538 A | 10/2000 | Fischell et al. | |
| 6,136,021 A | 10/2000 | Tockman et al. | |
| 6,141,576 A | 10/2000 | Littmann et al. | |
| 6,152,899 A | 11/2000 | Farley et al. | |
| 6,161,029 A | 12/2000 | Spreigl et al. | |
| 6,161,047 A | 12/2000 | King et al. | |
| 6,170,488 B1 | 1/2001 | Spillman, Jr. et al. | |
| 6,179,858 B1 | 1/2001 | Squire et al. | |
| 6,192,279 B1 | 2/2001 | Barreras, Sr. et al. | |
| 6,192,280 B1 | 2/2001 | Sommer et al. | |
| 6,205,361 B1 | 3/2001 | Kuzma et al. | |
| 6,216,045 B1 | 4/2001 | Black et al. | |
| 6,231,516 B1 | 5/2001 | Keilman et al. | |
| 6,249,707 B1 | 6/2001 | Kohnen et al. | |
| 6,263,248 B1 | 7/2001 | Farley et al. | |
| 6,266,568 B1 | 7/2001 | Mann et al. | |
| 6,292,702 B1 | 9/2001 | King et al. | |
| 6,319,241 B1 * | 11/2001 | King et al. | 604/502 |
| 6,319,251 B1 | 11/2001 | Tu et al. | |
| 6,330,477 B1 | 12/2001 | Casavant | |
| 6,353,762 B1 | 3/2002 | Baudino et al. | |
| 6,360,122 B1 | 3/2002 | Fischell et al. | |
| 6,361,528 B1 | 3/2002 | Wilson et al. | |
| 6,370,427 B1 | 4/2002 | Alt et al. | |
| 6,391,052 B2 | 5/2002 | Buirge et al. | |
| 6,391,643 B1 | 5/2002 | Chen et al. | |
| 6,393,325 B1 | 5/2002 | Mann et al. | |
| 6,397,109 B1 | 5/2002 | Cammilli et al. | |
| 6,402,746 B1 | 6/2002 | Whayne et al. | |
| 6,408,214 B1 | 6/2002 | Williams et al. | |
| 6,415,187 B1 | 7/2002 | Kuzma et al. | |
| 6,418,344 B1 | 7/2002 | Rezai et al. | |
| 6,430,442 B1 | 8/2002 | Peters et al. | |
| 6,438,427 B1 | 8/2002 | Rexhausen et al. | |
| 6,442,413 B1 | 8/2002 | Silver | |
| 6,442,435 B2 * | 8/2002 | King et al. | 607/117 |
| 6,445,953 B1 | 9/2002 | Bulkes et al. | |
| 6,463,328 B1 | 10/2002 | John | |
| 6,466,822 B1 | 10/2002 | Pless | |
| 6,480,743 B1 | 11/2002 | Kirkpatrick et al. | |
| 6,484,059 B2 | 11/2002 | Gielen | |
| 6,510,347 B2 | 1/2003 | Borkan | |
| 6,516,227 B1 | 2/2003 | Meadows et al. | |
| 6,519,488 B2 | 2/2003 | KenKnight et al. | |
| 6,522,932 B1 | 2/2003 | Kuzma et al. | |
| 6,529,774 B1 * | 3/2003 | Greene | 600/545 |
| 6,539,263 B1 | 3/2003 | Schiff et al. | |
| 6,547,788 B1 | 4/2003 | Maguire et al. | |
| 6,547,870 B1 | 4/2003 | Griessmann et al. | |
| 6,562,063 B1 | 5/2003 | Euteneuer et al. | |
| 6,584,358 B2 | 6/2003 | Carter et al. | |
| 6,587,733 B1 | 7/2003 | Cross, Jr. et al. | |
| 6,589,230 B2 | 7/2003 | Gia et al. | |
| 6,591,138 B1 | 7/2003 | Fischell et al. | |
| 6,597,953 B2 | 7/2003 | Boling | |
| 6,600,954 B2 | 7/2003 | Cohen et al. | |
| 6,600,956 B2 | 7/2003 | Maschino et al. | |
| 6,606,521 B2 | 8/2003 | Paspa et al. | |
| 6,625,496 B1 | 9/2003 | Ollivier | |
| 6,647,296 B2 | 11/2003 | Fischell et al. | |
| 6,658,302 B1 | 12/2003 | Kuzma et al. | |
| 6,662,055 B1 | 12/2003 | Prutchi | |
| 6,665,562 B2 | 12/2003 | Gluckman et al. | |
| 6,671,544 B2 | 12/2003 | Baudino | |
| 6,675,046 B2 | 1/2004 | Hosheimer | |
| 6,690,974 B2 | 2/2004 | Archer et al. | |
| 6,697,676 B2 | 2/2004 | Dahl et al. | |
| 6,714,822 B2 | 3/2004 | King et al. | |
| 6,837,886 B2 | 1/2005 | Collins et al. | |
| 6,842,648 B2 | 1/2005 | Partridge et al. | |
| 6,895,283 B2 | 5/2005 | Erickson et al. | |
| 6,909,918 B2 | 6/2005 | Stypulkowski | |
| 6,959,820 B2 | 11/2005 | Koslow | |
| 6,988,007 B1 | 1/2006 | Morgan et al. | |
| 6,999,820 B2 | 2/2006 | Jordan | |
| 7,072,719 B2 | 7/2006 | Vinup et al. | |
| 7,349,743 B2 * | 3/2008 | Tadlock | 607/116 |

| 7,561,924 B2 | 7/2009 | Kolberg et al. |
| 2001/0025192 A1 | 9/2001 | Gerber et al. |
| 2001/0041821 A1 | 11/2001 | Wilk |
| 2001/0053885 A1 | 12/2001 | Gielen et al. |
| 2002/0026228 A1 | 2/2002 | Schauerte |
| 2002/0111618 A1* | 8/2002 | Stewart et al. .......... 606/41 |
| 2002/0111661 A1 | 8/2002 | Cross et al. |
| 2002/0151948 A1 | 10/2002 | King et al. |
| 2002/0151949 A1 | 10/2002 | Dah et al. |
| 2002/0156513 A1 | 10/2002 | Borkan |
| 2002/0183791 A1 | 12/2002 | Denker et al. |
| 2002/0188207 A1 | 12/2002 | Richter |
| 2003/0014016 A1 | 1/2003 | Purdy |
| 2003/0040785 A1 | 2/2003 | Maschino et al. |
| 2003/0199962 A1 | 10/2003 | Struble et al. |
| 2003/0204135 A1 | 10/2003 | Bystritsky |
| 2003/0204228 A1 | 10/2003 | Cross et al. |
| 2004/0015193 A1 | 1/2004 | Lamson et al. |
| 2005/0004639 A1 | 1/2005 | Erickson |
| 2005/0137646 A1 | 6/2005 | Wallace et al. |
| 2005/0149156 A1 | 7/2005 | Libbus et al. |
| 2006/0161246 A1 | 7/2006 | Rhim et al. |

FOREIGN PATENT DOCUMENTS

| EP | 0 864 800 A2 | 9/1998 |
| EP | 0 865 800 A2 | 9/1998 |
| EP | 0861676 | 9/1998 |
| EP | 0 864 800 A3 | 12/1999 |
| EP | 0 865 800 A3 | 12/1999 |
| EP | 0 864 800 B1 | 9/2004 |
| EP | 0865800 B1 | 9/2004 |
| WO | WO 01/85094 | 11/2001 |
| WO | WO 03/077986 | 9/2003 |

OTHER PUBLICATIONS

Onal, Cagatay, et al., "Complications of Invasive Subdural Grid Monitoring in Children with Epilepsy," J. Neurosurg. 98: pp. 1017-1026, 2003.

IP.com: Electrotrode Design to Stimulate Blood Vessels, Nerves, or Other Tubular Organs, file://C:\unzipped\IPCOM000010247D1\0_properties.xml, Published Nov. 13, 2002.

IP.com: Epidural Needle for Spinal Cord Stimulation Electrode, file://C:unzipped\IPCOM000011384D1\0_properties.xml, Published Feb. 14, 2003.

IP.com: Medical Lead System and Method for Insertion into the Spinal Cord, file://C:\unzipped\IPCOM000011389D1\0_properties.xml, Published Feb. 17, 2003.

IP.com: Transcutaneous Screening Test for Evaluation of Potential Efficacy of Chronic Trigeminal Neurostimulation as a Therapy for Epilepsy, file://C:\unzipped\IPCOM000011987D1\0_properties.xml, Published Mar. 28, 2003.

IP.com: System and Method for Lead Fixation, file://C:\unzipped\IPCOM000019571D1\0_properties.xml, Published Sep. 19, 2003.

IP.com: Dual Lumen Inflatable Lead, file://C:\unzipped\IPCOM000019703D1\0_properties.xml, Published Sep. 25, 2003.

IP.com: Skull-Mounted Electrical Stimulation System, file://C:\unzipped\IPCOM000019827D1\0_properties.xml, Published Oct. 1, 2003.

IP.com: Spinal Cord Stimulation as a Therapy for Epilepsy, file://C:\unzipped\IPCOM000019881D1\0_properties.xml, published Oct. 6, 2003.

IP.com: Skull-Mounted Electrical Stimulation System and Method for Treating Patients, file://C:\unzipped\IPCOM000021554D1\0_properties.xml, Published Jan. 22, 2004.

Canavero, Sergio et al., "Extradural Motor Cortex Stimulation for Advanced Parkinson Disease," J. Neurosurg. 97: pp. 1208-1211, 2002.

Kunieda, Takeharu et al., "Use of Cavernous Sinus EEG in the Detection of Seizure Onset and Spread in Mesial Temporal Lobe Epilepsy," Epilepsia, 41(11): pp. 1411-1419, 2000.

Onal, Cagatay, et al. "Complications of Invasive Subdural Grid Monitoring in Children with Epilepsy," J. Neurosurg. 98: pp. 1017-1026, 2003.

PCT International Search Report for PCT/US2005/010121, Applicant: Boston Scientific Scimed, Inc., Forms PCT/ISA/210 and 220, dated Jul. 4, 2005 (7 pages).

PCT Written Opinion of the International Search Authority for PCT/US2005/010121, Applicant: Boston Scientific Scimed, Inc., Form PCT/ISA/237, dated Jul. 4, 2005 (5 pages).

PCT International Search Report for PCT/US2005/006569, Applicant: Boston Scientific Scimed, Inc., Forms PCT/ISA/210 and 220, dated Jun. 13, 2005 (7 pages).

PCT Written Opinion of the International Search Authority for PCT/US2005/006569, Applicant: Boston Scientific Scimed, Inc., Form PCT/ISA/237, dated Jun. 2005 (5 pages).

Web Article: IP.com: "Dual Lumen Inflatable Lead." File://c:\unzipped \IPCOM000019703D1\0_properties.xml, Published Sep. 25, 2003 (7 pages).

Web Article: IP.com: "Electrode Design to Stimulate Blood Vessels, Nerves, or Other Tubular Organs." File://c\unzipped\IPCOM000010247D1\0_properties.xml, Published Nov. 13, 2002 (13 pages).

Web Article: IP.com: "Epidural Needle for Spinal Cord Stimulation Electrode." File://c:\unzipped\IPCOM000011384D1\0_properties.xml, Published Feb. 14, 2003 (6 pages).

Web Article: IP.com: "Medical Lead System and Method for Insertion into the Spinal Cord." File://c:\unzipped\IPCOM000011389D1\0_properties.xml, Published Feb. 17, 2003 (7 pages).

Web Article: IP.com: "Methods and Placement of Neurostimulation Lead, Infusion Catheter, and/or Sensor Via the Vasculature to the Brain." IPCOM000012135D, Published Apr. 10, 2003 (11 pages).

Web Article: IP.com: "Methods of Placement of Neurostimulation Lead, Infusion Catheter, and/or Sensor Via Peripheral Vasculature." 0349945-003 (7 pages).

Web Article: IP.com: "Skull-Mounted Electrical Stimulation System." File://c:\unzipped\IPCOM000019827D1\0_properties.xml, Published Oct. 1, 2003 (29 pages).

Web Article: IP.com: "Skull-Mounted Electrical Stimulation System and Method for Treating Patients." File://c:\unzipped\IPCOM000021554D1\0_properties.xml, Published Jan. 22, 2004 (31 pages).

Web Article: IP.com: "Spinal Cord Stimulation as a Therapy for Epilepsy." File://c:\unzipped\IPCOM000019881D1\0_properties.xml, Published Oct. 6, 2003 (10 pages).

Web Article: IP.com: "System and Method for Lead Fixation." File://c:\unzipped\IPCOM000019571D1\0_properties.xml, Published Sep. 19, 2003 (11 pages).

Web Article: IP.com: "Transcutaneous Screening Test for Evaluation of Potential Efficacy of Chronic Trigeminal Neurostimulation as a Therapy for Epilepsy." File://c:\unzipped\IPCOM000011987D1\0_properties.xml, Published Mar. 28, 2003 (8 pages).

Extended European Search Report dated Dec. 19, 2008 in EP Application No. 08017295.0-1265; (5 pages).

PCT International Search Report and the Written Opinion for PCT/US2005/007179, Applicant: Boston Scientific Scimed, Inc., Forms PCT/ISA/210, 220, and 237, dated Jun. 24, 2005. (11 pages).

Office Action dated Apr. 16, 2008 for related U.S. Appl. No. 10/799,271, filed Mar. 12, 2004, Inventor: Robert J. Garabedian (22 pages).

* cited by examiner

US 7,937,160 B2

METHODS FOR DELIVERING CORTICAL ELECTRODE LEADS INTO PATIENT'S HEAD

FIELD OF THE INVENTION

The invention relates to the treatment and diagnosis of physiological disorders, and in particular, the treatment and diagnosis of physiological disorders using electrical brain stimulation.

BACKGROUND OF THE INVENTION

It is sometimes desirable to treat disorders in patients using implantable electrical stimulation leads. For example, it is known to treat the adverse effects of neurological disorders, such as Parkinson's disease and epilepsy, and most recently, to rehabilitate stroke patients, by electrically stimulating the motor/pre-motor regions of the patient's cortical brain tissue with one or more paddle-like stimulation leads. Access to the patient's brain is accomplished using a fairly invasive procedure, which involves either drilling multiple burr holes through the patient's cranium or performing a craniotomy on the patient.

If a craniotomy is the selected means for accessing the patient's brain, the stimulation leads are merely inserted through the large opening in the cranium and placed into their proper positions along the cortex. The portion of the patient's cranium that was removed during the craniotomy is then placed back and secured within its original position in the cranium.

If burr holes are the selected means for accessing the patient's brain, each stimulation lead is inserted through one of the burr holes and advanced towards another burr hole. A medical implement is inserted into the other burr hole and used to pull or otherwise manipulate the lead into proper position along the cortex. Although the use of burr holes is generally less invasive than a craniotomy, the size of burr holes are still relatively large—typically around 15 mm in diameter, in order to accommodate the high-profile paddle-like leads and medical implements.

There, thus, remains a need to provide improved methods and kits for delivering electrodes leads within a patient's head between the cranium and cortical brain tissue of the patient.

SUMMARY OF THE INVENTION

In accordance with one aspect of the present inventions, a method of delivering an electrode lead into the head of a patient is provided. The method comprises forming a burr hole within the cranium of the patient. To minimize the invasiveness of the procedure, the burr hole is preferably as small as possible, e.g., 2-3 millimeters. The method further comprises linearly introducing the electrode lead through the burr hole, and placing the electrode lead in a pre-shaped two-dimensional geometry between the cranium and cortical brain tissue of the patient. In one method, the electrode lead is placed between the dura mater that protects the cortical brain tissue and the cranium. The electrode lead may be, e.g., an electrical stimulation lead, in which case, it can be electrically coupled to an electrical stimulation source. Stimulation energy can then be conveyed from the stimulation source to the stimulation lead and into the cortical brain tissue to treat a disorder. In other methods, the electrical lead may be a sensing lead for recording brain signals. The method may optionally comprise mounting an access anchor into the burr hole, and then introducing the electrode lead though the access anchor. The access anchor can then be used to electrically couple an extension lead, which may be routed outside of the patient's head to the stimulation source or other device, to the electrode lead.

The electrode lead may be placed into the two-dimensional geometry between the cortical brain tissue and the cranium in any one of a number of ways. For example, the electrode lead can be advanced between the cranium and the cortical brain tissue during which the electrode is automatically placed into the two-dimensional geometry. This can conveniently be accomplished by pre-shaping the stimulation into a coil that outwardly winds as the electrode lead is introduced through the burr hole. Alternatively, the electrode lead can be introduced through the burr hole with a sheath, in which case, the sheath can be removed from the electrode lead to place it into the two-dimensional geometry. In this case, the electrode lead may be pre-shaped, e.g., in an meandering or branched fashion. In any event, the electrode lead can be urged into the two-dimensional geometry via an integrated center support or by a stylet that can then be removed from the electrode lead after the two-dimensional geometry has been assumed.

In some situations it may be desirable to detect the leakage of fluids, such as cerebral spinal fluid (CSF) or blood from the patient's head. In this case, the electrode lead may have a monitoring lumen that aspirates any fluid from between the cranium and the cortical brain tissue and/or allows a scope to be inserted therethrough into the patient's head to visualize any fluid. In some circumstances, e.g., when operating on an elderly patient, it may be desirable to separate the dura mater overlying the cortical brain tissue from the cortical brain tissue to create a pocket in which the electrode lead may be manipulated. In this case, a tissue layer dissection device can be introduced through the burr hole, operated to separate the dura mater from the cranium, and then removed from the burr hole. In one embodiment, the dissection device comprises a balloon that can be inflated to separate the dura mater and cranium, and then deflated prior to removing the dissection device from the burr hole.

In accordance with a second aspect of the present inventions, another method of delivering an electrode lead into the head of a patient is provided. The method comprises introducing a balloon through the burr hole, inflating the balloon to create a pocket between the dura mater and cranium of the patient, deflating the balloon, and removing the balloon from burr hole. An electrode lead is then introduced through the burr hole and placed within the pocket. The electrode lead may have the same structure and function, and delivered in the same manner, as the electrode leads described above, or alternatively, may be a standard cortical brain tissue electrode lead that is delivered in a standard manner through the burr hole.

In accordance with a third aspect of the present inventions, a cortical brain tissue electrode kit is provided. The kit comprises an access anchor configured for being mounted in a burr hole formed in the cranium of a patient. The access anchor may comprise threads to facilitate mounting in the burr hole when the access anchor is rotated. In this case, a tool can be used to rotate the access anchor within the burr hole. The kit further comprises an electrode lead configured for being linearly delivered through the access anchor and placed in a pre-shaped two-dimensional geometry between the cranium and cortical brain tissue of the patient. The electrode lead may have the same structure and function as the electrode leads described above. The kit may optionally comprise an electrical stimulation source configured for delivering stimulation energy to the stimulation lead. The kit may also optionally comprise a tissue layer dissection device configured for being introduced through the access anchor and operated to separate the dura mater overlying the cortical brain tissue from the cranium. This dissection device may have the same structure as that of the dissection device described above.

In accordance with a fourth aspect of the present inventions, another cortical brain tissue electrode kit is provided. The kit comprises an access anchor configured for being mounted in a burr hole formed in the cranium of a patient. The access anchor can have the same structure as the previously described access anchor. The kit further comprises a balloon configured for being alternately placed between a deflated state for delivery through the access anchor, and an inflated state for separating dura tissue from the cranium to form a pocket. The kit also comprises an electrode lead configured for being advanced through the access anchor and into the pocket. The electrode lead can have the same structure and function as the electrode leads described above, or alternatively, may be a standard cortical brain tissue electrode lead.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which.

DETAILED DESCRIPTION OF THE PREFERRED EMBODIMENTS

Figure 1:
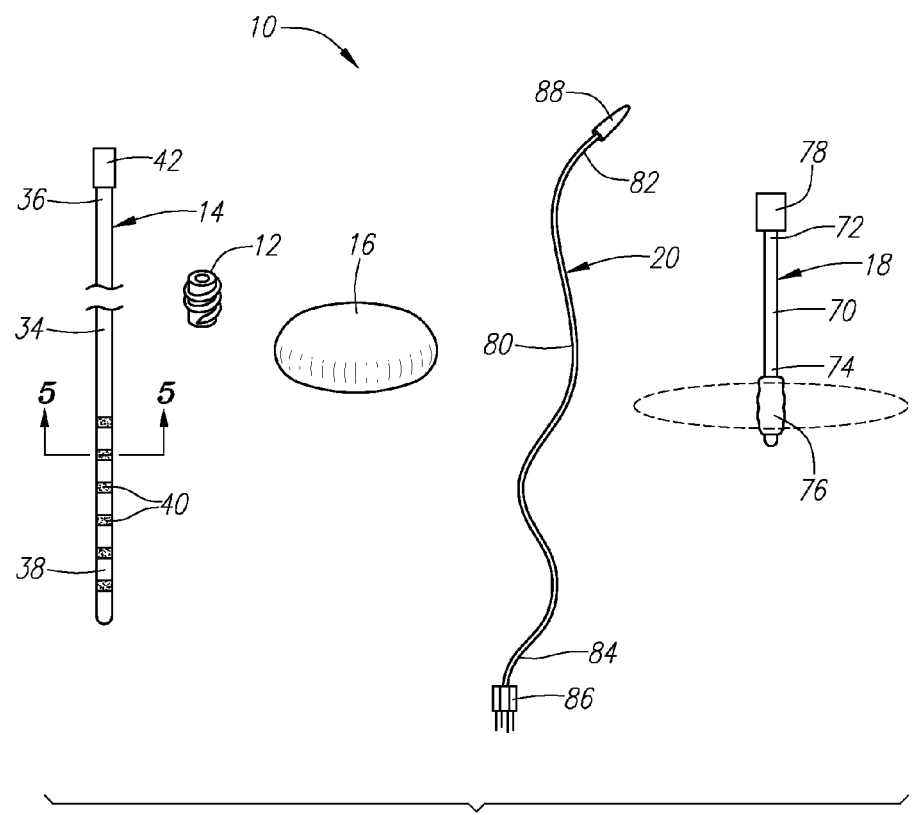
FIG. 1 is a plan view of a cortical brain tissue stimulation kit arranged in accordance with a preferred embodiment of the present invention.

Referring now to FIG. 1, a cortical brain tissue stimulation kit 10 constructed in accordance with one preferred embodiment of the present invention is shown. The kit 10 can be used to stimulate cortical brain tissue in order to treat disorders, such as Parkinson's disease, epilepsy, and stroke, or the effects thereof. In its simplest form, the kit 10 generally comprises an access anchor 12 for providing convenient access to the patient's cortical brain tissue, an electrode lead, and in particular, a stimulation lead 14 for electrically stimulating the cortical brain tissue, and an implantable stimulation source 16 for providing stimulation energy to the stimulation lead 14. The kit 10 also comprises an optional tissue layer dissection device 18 for separating the dura mater from the cranium of the patient in order to form a pocket in which the stimulation lead 14 can be manipulated, as well as an optional extension lead 20 for electrically coupling the implanted stimulation source 16 to the stimulation lead 14.

Figure 2:
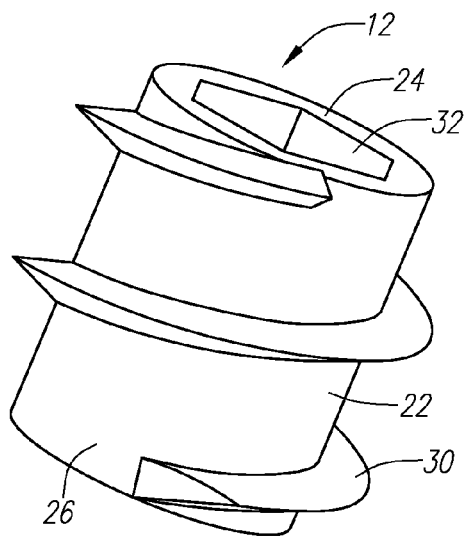
FIG. 2 is a side perspective view of an access anchor used in the kit of FIG. 1.
Figure 3:
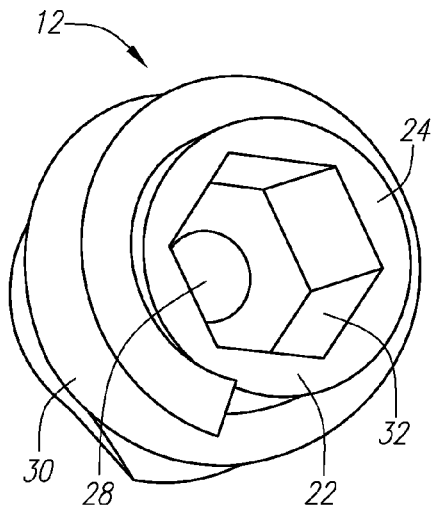
FIG. 3 is a proximal perspective view of the access anchor of FIG. 2.
Figure 4:
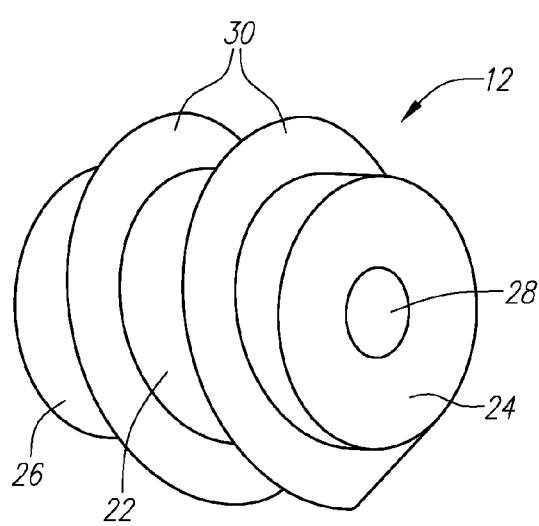
FIG. 4 is a distal perspective view of the access anchor of FIG. 2.

Referring further to FIGS. 2-4, the access anchor 12 is configured for being mounted in a burr hole formed in the cranium of the patient. In the illustrated embodiment, the burr hole in which the access anchor 12 is mounted is as small as possible, e.g., 2-3 millimeters in diameter, in contrast to prior art burr holes, which were on the order of 15 millimeters in diameter. To this end, the access anchor 12 comprises a generally cylindrical rigid body 22 having a proximal end 24 and a distal end 26. The diameter of the rigid body 22 is preferably approximately equal to that of the burr hole. The rigid body 22 may be composed of any suitable rigid and biocompatible material, such as stainless steel, titanium, metallic alloy, polysulfone, urethane, or polyimide. Preferably, however, the rigid body 22 is composed of an electrically non-conductive material in order to provide a robust means of electrical insulation between the stimulation lead 14 and the optional extension lead 20, as will be described in further detail below.

The access anchor 12 further comprise a port 28 that extends through the entire length of the rigid body 22. As will be described in further detail below, the port 28 can be used to deliver and remove the stimulation lead 14, optional tissue layer dissection device 18, and other therapeutic and/or diagnostic devices to and from the patient's head as necessary. The access anchor 12 further comprises self-tapping threads 30 disposed on the exterior of the rigid body 22, so that the access anchor 12 will firmly anchor itself within the burr hole when rotated around its longitudinal axis. It can be appreciated that the diameter of the threads 30 is greater than the diameter of the burr hole, so that the threads 30 etch themselves into the bone tissue surrounding the burr hole when the access anchor 12 is mounted.

To facilitate torqueing of the access anchor 12 within the burr hole, the access anchor 12 also comprises a driven mechanism 32 that can be used to facilitate its rotation within the burr hole. In the illustrated embodiment, the driven mechanism 32 takes the form of a hexagonal recess formed at the proximal end of the rigid body 22. A driver mechanism, such as an alien wrench (not shown), can be inserted into the hexagonal recess 32 and torqued in order to rotate the access anchor 12 against the frictional resistance exerted by the bone tissue. The hexagonal recess 32 also functions as a female connector for the extension lead 20, as will be described in further detail below.

Figure 5:
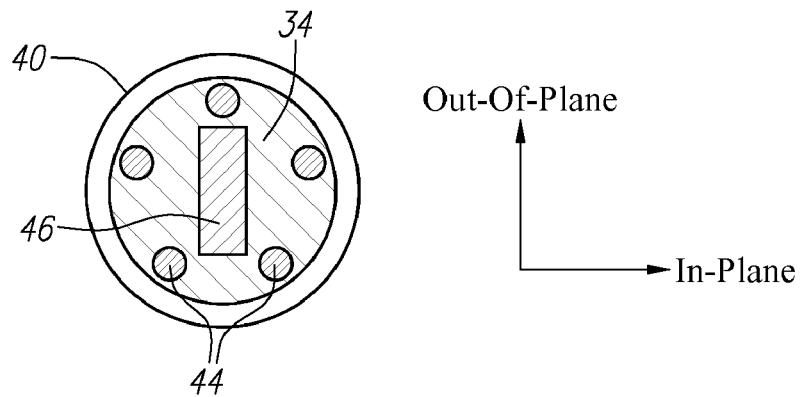
FIG. 5 is a cross-sectional view of one embodiment of a pushable stimulation lead used in the kit of FIG. 1, taken along the line 5-5.

Referring to FIGS. 1 and 5, the stimulation lead 14 comprises an elongated tubular body 34 having a proximal end 36 and a distal end 38. The tubular body 34 is composed of a suitably flexible material (such as polyurethane, polyethylene, silicone, PEBAX®, etc.), which may either be resilient or non-resilient, and may be formed via an extrusion process or by any other suitable means. In the illustrated embodiment, the tubular body 34 is cylindrically-shaped, but may have other cross-sectional geometries, such as oval, rectangular, triangular, etc.

The stimulation lead 14 further comprises a plurality of segmented electrodes 40 mounted along the distal end 38 of the elongated tubular body 34, and a connector 42 mounted on the proximal end 36 of the tubular body 34. The electrodes 40 are electrically coupled to the connector 42 via signal wires 44 extending through the tubular body 34. The stimulation lead 14 may be arranged such that signals can be independently transmitted to the electrodes 40 either in a monopolar or bipolar arrangement, in which case, the stimulation lead will have multiple channels, or may be arranged such that a signal is simultaneously transmitted to multiple electrodes. The segmented electrodes 40 may comprise, e.g., solid rings of a biocompatible and electrically conductive material, such as platinum, copper alloy, stainless steel, or nitinol. The electrically conducting material of the electrodes 40 can be further coated with platinum-iridium or gold to improve their conduction properties, biocompatibility, and radiopacity. As will be described in further detail below, the connector 42 is shaped and sized to be interference fitted within the port 28 of the access anchor 28, such as, e.g., using a snap-fit configuration.

Figure 6:
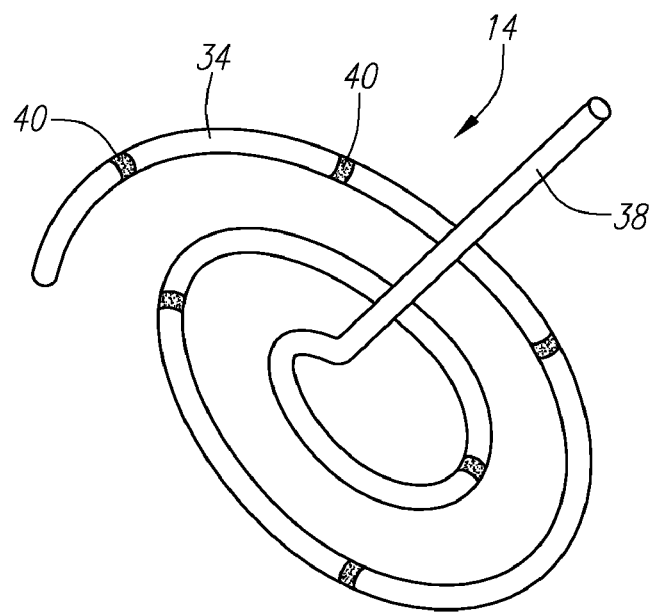
FIG. 6 is a perspective view of the expanded distal end of the pushable stimulation lead of FIG. 1.

The stimulation lead 14 is configured for being linearly delivered through the access anchor port 28. To this end, the outer diameter of the tubular body 34 is slightly smaller than the diameter of the access anchor port 28, so that the stimulation lead 14 can more easily pass in and out of the port 28. The stimulation lead 14 is also configured for being expanded into a pre-shaped two-dimensional geometry, as illustrated in FIG. 6, which for the purposes of this specification, is any geometry that is planar or curviplanar. To provide this pre-shaped geometry, the stimulation lead 14 comprises a pre-shaped resilient center support 46 that extends through the tubular body 34 in a fixed manner and urges the stimulation lead 14 into the two-dimensional geometry. The center support 46 also provides the stimulation lead 14 with axial rigidity to facilitate its introduction through the access anchor 12 and between the patient's cortical brain tissue and cranium, and in particular, between the dura mater covering the cortical brain tissue and the cranium. The center support 46 may be composed of any relatively stiff and resilient material, such as stainless steel, a metallic and polymer material, or a high-stiffness urethane or silicone, that is shaped into the desired geometry. In alternative embodiments, the center support 46 may be composed of a shape memory material, such as nitinol, so that it assumes the desired geometry in the presence of a defined temperature, such as, e.g., body temperature.

In the embodiment illustrated in FIG. 6, the stimulation lead 14 is configured as a pushable design, meaning that as the stimulation lead 14 is introduced through the access anchor 12, the distal end 38 of the stimulation lead 14 will expand into its two-dimensional geometry between the dura mater and cranium. In order to facilitate this expansion, the two-dimensional geometry assumed by the expandable distal end 38 of the stimulation lead 14 is a coil that outwardly winds over the dura mater as the stimulation lead 14 is advanced through the access anchor 12, as will be described in further detail below. As illustrated in FIG. 5, the cross-section of the center support 46 is rectangular, with the longer edges of the cross-section being orientated out-of-plane and the shorter edges of the cross-section being in-plane, so that the coil more easily winds in-plane between the cortical tissue and cranium of the patient. In order to minimize the mechanical stress between the expandable distal end 38 of the stimulation lead 14 and the remaining region of the stimulation lead 14, which is configured to extend up into the access anchor 12 from the cortical brain tissue, the expandable distal end 38 of the stimulation lead 14 is pre-shaped to lie in a plane that is orthogonal to the proximal end of the stimulation lead 14.

Figure 7:
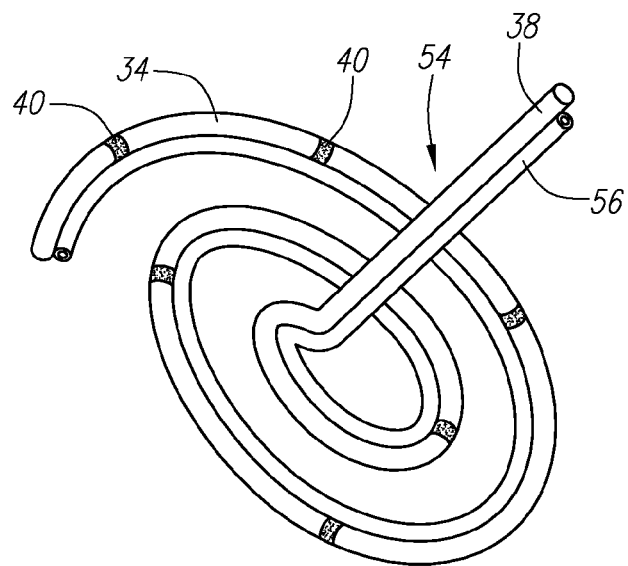
FIG. 7 is a perspective view of the expanded distal end of another embodiment of the pushable stimulation lead of FIG. 1.

Referring now to FIG. 7, an alternative embodiment of a stimulation lead 54 is illustrated. The stimulation lead 54 is similar to the previously described stimulation lead 14, with the exception that it includes a monitoring lumen 56 that can be used to aspirate blood or cerebral spinal fluid (CSF) from the patient's head or introduce a small diameter scope (not shown) within the patient's head. In this manner, leakage of CSF, or worse yet, leakage of blood, can be monitored, and remedial measures can be taken if necessary. In the embodiment illustrated in FIG. 7, the monitoring lumen 56 externally extends down one side of the tubular body 34. The monitoring lumen 56 can be formed onto the tubular body 34 in any suitable manner, for example, bonding the monitoring lumen 56 to the side of the tubular body 34, or coextruding the tubular body 34 and monitoring lumen 56 together.

Figure 8:
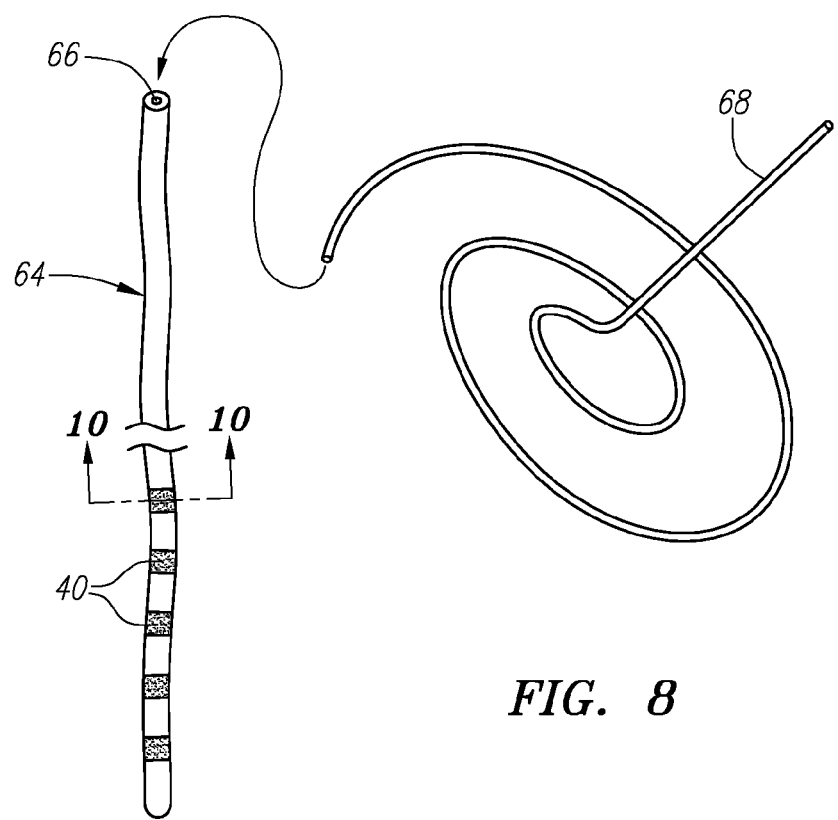
FIG. 8 is an exploded perspective view of the expanded distal end of still another embodiment of the pushable stimulation lead of FIG. 1.
Figure 9:
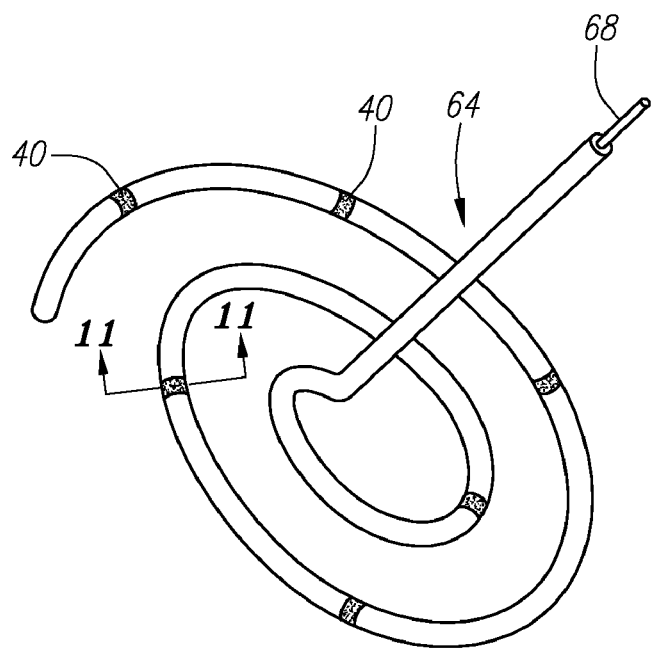
FIG. 9 is an integrated perspective view of the expanded distal end of the pushable stimulation lead of FIG. 8.
Figure 10:
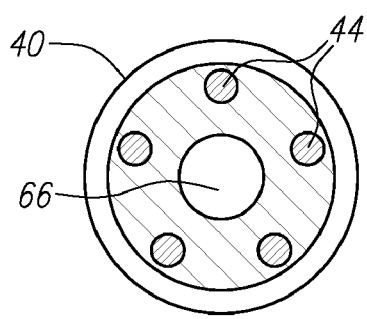
FIG. 10 is a cross-sectional view of the stimulation lead of FIG. 8, taken along the line 10-10.
Figure 11:
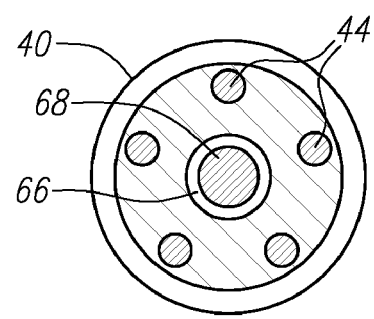
FIG. 11 is a cross-sectional view of the stimulation lead of FIG. 9, taken along the line 11-11.

It should be noted that the use of an external monitoring lumen, such as that illustrated in FIG. 7, increases the profile of the stimulation lead 54, which may disadvantageously result in an increase in the burr hole in which the access anchor 12 is mounted. Alternatively, as illustrated in FIGS. 8 and 9, a stimulation lead 64 with an internal monitoring lumen can be used. The stimulation lead 54 is similar to the previously described stimulation lead 14, with the exception that, rather than a fixed center support 46, it comprises an internal monitoring lumen 66 and a stilette 68 removably disposed within the monitoring lumen 66. The stilette 68 can be composed of the same material and be pre-shaped in the same manner as the center support 46. Thus, it can be appreciated that the stilette 68 can be inserted into the monitoring lumen 66 in order to facilitate introduction of the stimulation lead 64 through the access anchor 12 and expansion of the distal end of the stimulation lead 64 into the desired two-dimensional geometry, in this case, a coil. The stilette 68 can be removed from the monitoring lumen 66, after which, the empty monitoring lumen 66 may serve either as an aspiration lumen or as a means for introducing the small bore scope into the patient's head for detection of any CSF or blood leaks. As illustrated in FIGS. 10 and 11, the cross-section of the monitoring port 28, as well as the stilette 68, is circular, in order to facilitate introduction of the bore scope, which will typically have a circular cross-section.

The afore-described monitoring lumens can also be used to introduce other devices or agents into the patient's head. For example, the monitoring lumens can be used to perform functional mapping using voltage or current sensing dyes, direct spectroscopy, or indirect optical measurement of physiological parameters, such as oxy- to deoxyhemogoblin transitions. This will produce convergent information used to enhance physiological mapping of regions, such as eloquent neocortex or areas of pathophysiology like epileptic foci, or dysgenic cortex.

Although the stimulation leads described up to this point have been pushable, stimulation leads can also be configured as a sheath design, meaning that the stimulation lead is configured to be introduced through the access anchor 12 using a sheath that maintains the stimulation lead in a collapsed or linear geometry, while providing the axial strength necessary to manipulate the stimulation lead between the dura mater and cranium. The sheath can then be pulled back to deploy or place the stimulation lead into an expanded two-dimensional geometry between the dura mater and cranium.

Figure 12:
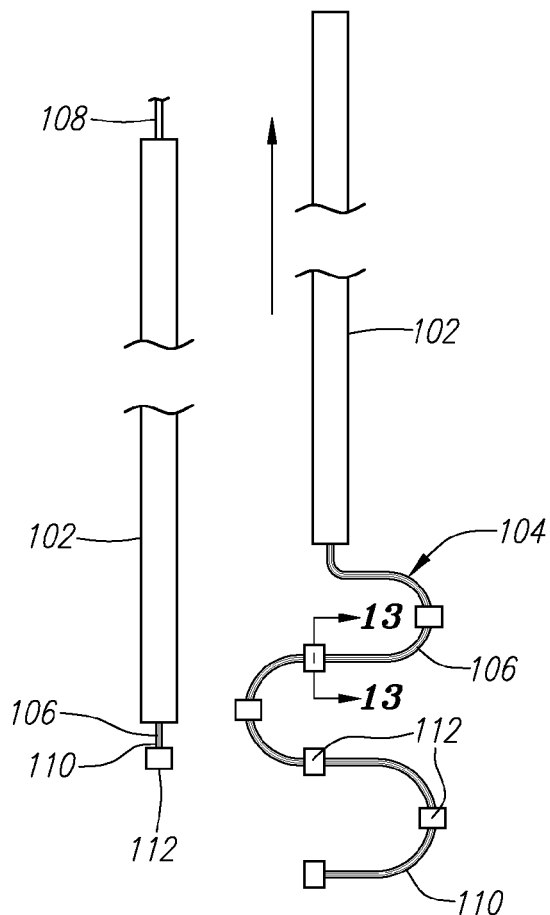
FIG. 12 is a plan view of an alternative embodiment of a sheathed stimulation lead that can be used in the kit of FIG. 1, particularly showing expansion of the distal end of the stimulation lead.

For example, FIG. 12 illustrates one embodiment of a stimulation lead 104 that can be delivered through the access anchor 12 with a sheath 102. The stimulation lead 104 comprises a spring element 106 having a proximal end 108 and a distal end 110, a plurality of electrodes 112 mounted along the distal end 110 of the spring element 106, and a connector 112 mounted on the proximal end 108 of the spring element 106. The electrodes 112 are electrically coupled to the connector 42 via insulated signal wires 114 (shown in FIG. 13) extending through the spring element 106. The stimulation lead 104 may be arranged such that signals can be independently transmitted to the electrodes 112 either in a monopolar or bipolar arrangement, in which case, the stimulation lead 104 will have multiple channels, or may be arranged such that a signal is simultaneously transmitted to multiple electrodes. In any event, the spring element 106 comprises an electrically insulative layer (not shown) between the electrodes 112 in order to electrically isolate the electrodes 112. The electrodes 112 can be formed onto the spring element 106 using known deposition processes, such as sputtering, vapor deposition, ion beam deposition, electroplating over a deposited seed layer, or a combination of these processes. Or the electrodes can be discrete elements that are suitably mounted to the spring element 106. The electrodes 112 may be composed of the same material as the previously described segmented electrodes 112.

Figure 13:
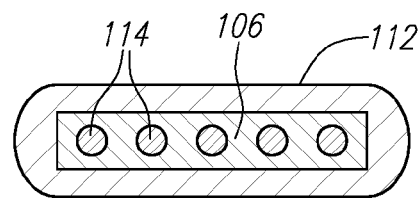
FIG. 13 is a cross-sectional view of the sheathed stimulation lead of FIG. 12, taken along the line 13-13.

The spring element 106 is composed of any relatively stiff and resilient material, such as stainless steel, a metallic and polymer material, or a high-stiffness urethane or silicone, that is shaped into the desired geometry. In alternative embodiments, the spring element 106 may be composed of a shape memory material, such as nitinol, so that it assumes the desired geometry in the presence of a defined temperature, such as, e.g., body temperature. As shown in FIG. 13, the spring element 106 has a planar geometry in that it has a minimal thickness (height) as compared to its width. As a result, the stimulation lead 104 may be more easily manipulated between the cortical brain tissue and cranium. Alternatively, the spring element 106 can be made from wire, which is cylindrical in nature.

As can be seen in FIG. 12, the spring element 106 is formed of a single linear element that longitudinally extends in a meandering fashion. In this case, the laterally extending curves of the meandering spring element 106 provide the necessary spring force to urge the distal end of the stimulation lead 104 from its low-profile collapsed geometry into an expanded two-dimensional geometry. Due to the meandering nature of the spring element 106, the stimulation lead 104 lacks pushability. As such, the sheath 102 is used to deliver the stimulation lead 104, in its collapsed geometry, through the access anchor 12 and between the dura mater and cranium. The sheath 102 can then be removed to place the distal end of the stimulation lead 104 into its expanded geometry. The sheath 102 can be provided with an optional monitoring lumen (not shown) to detect any CSF or blood through aspiration or visualization with a scope.

Figure 14:
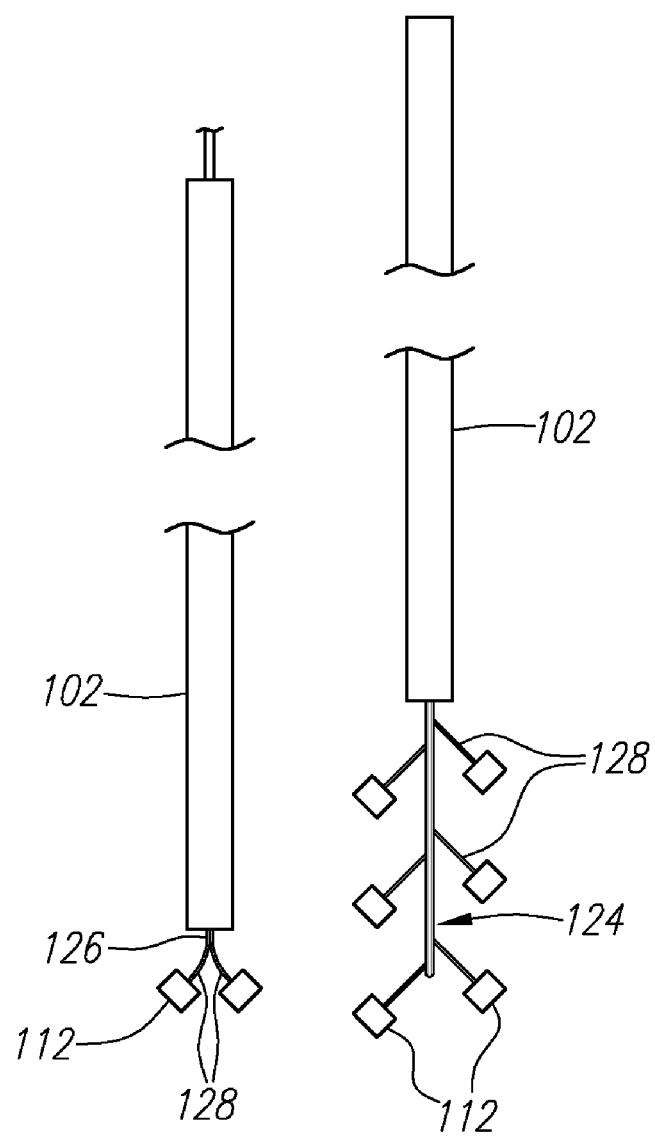
FIG. 14 is a plan view of another alternative embodiment of a sheathed stimulation lead that can be used in the kit of FIG. 1, particularly showing expansion of the distal end of the stimulation lead.

A sheath-type stimulation lead may have other expanded geometries besides the meandering geometry illustrated in FIG. 12. For example, FIG. 14 illustrates a stimulation lead 124 that is similar to the previously described stimulation lead 104, with the exception that it comprises a main spring element 126 that extends along a straight line and a plurality of lateral spring elements 128 that branch off of the main spring segment 124, with each lateral spring element 126 carrying an electrode 112. The lateral spring elements 126 act to provide the necessary spring force to urge the distal end of the stimulation lead 124 from its low-profile collapsed geometry into an expanded two-dimensional geometry. The sheath 102 can be used to deliver the stimulation lead 124, in its collapsed geometry, through the access anchor 12 and between the dura mater and cranium. The sheath 102 can then be removed to place the distal end of the stimulation lead 124 into its expanded geometry.

Returning to FIG. 1, the tissue layer dissection device 18 is configured to separate the dura mater from the cranium to create a pocket in which the stimulation lead 14 will be expanded. To this end, the dissection device 18 comprises an elongated shaft 70 having a proximal end 72 and a distal end 74, an expandable balloon 76 mounted to the distal end 74 of the shaft 70, and an inflation port 78 mounted to the proximal end 72 of the shaft 70. In the illustrated embodiment, the elongated shaft 70 is composed of a rigid material, such as stainless steel, but can alternatively be composed of a semi-rigid or flexible material. The inflation port 78 is in fluid communication with the interior of the balloon 76 via a lumen (not shown). In this manner, an inflation medium, such as saline, can be introduced through the inflation port 78 under pressure in order to expand the balloon 76 (as shown in phantom), and the inflation medium can be removed from the inflation port 78 to deflate the balloon 76.

As illustrated, the balloon 76, when expanded, assumes a planar-like radial geometry that resembles the shape of the intended pocket to be created, and in particular, the pocket between the dura mater and cranium. It can be appreciated that this planar-like pocket, while minimizing unnecessary displacement and trauma to surrounding tissue, such as the cortical brain tissue, provides the necessary space to allow navigation and expansion of the low-profile stimulation lead 14 within the patient's head. To further minimize unnecessary displacement and trauma to the cortical brain tissue, the balloon 76 is composed of a compliant material, such as silicone. However, the balloon 76 may be composed of a semi-compliant material, such as SELAR®, or a non-compliant material, such as PET, although additional care must be taken when expanding the balloon 76 within the patient's head. The tissue layer dissection device 18 may optionally comprise an external or internal monitoring lumen (not shown) similar to that incorporated into the tubular bodies of the stimulation lead 54, 64 illustrated in FIGS. 7 and 8. Thus, any leakage of CSF or blood caused by creation of the pocket can be detected via its aspiration through the monitoring lumen or a small-bore scope can be introduced through the monitoring lumen to visualize such leakage.

Figure 4A:
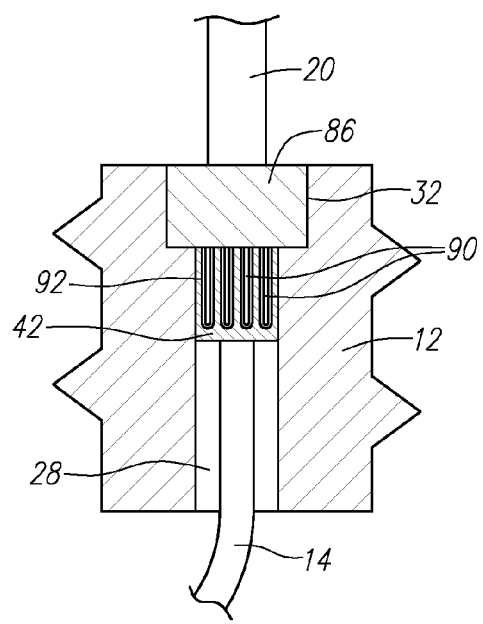
FIG. 4A is a cross-section view of the access anchor of FIG. 2, particularly showing the mating of lead connectors therein.

Referring still to FIG. 1, the extension lead 20 is configured to be coupled between the stimulation lead 14 via the access anchor 12 and the implantable stimulation source 16. To this end, the extension lead 20 comprises an electrically insulative sheath 80 having a proximal end 82 and a distal end 84, a distal connector 86 mounted on the distal end 84 of the sheath 80, a proximal connector 88 mounted on the proximal end 82 of the sheath 80, and wire conductors (not shown) that extend through the length of the sheath between the respective connectors 86, 88. As best shown in FIG. 4A, the distal connector 86 of the extension lead 20 is configured to mate with the connector 42 of the stimulation lead 14, which will be in a snap-fit arrangement with the port 28 of the access anchor 12.

To this end, the connector 86 has a hexagonal shape that allows it to be interference fit within the hexagonal recess 32 of the access anchor 12 using, e.g., a snap fit connection. The distal connector 86 of the extension lead 20 comprises pins 90 that are configured to be received into pin receptacles 92 within the connector 42 of the stimulation lead 14. The proximal connector 88 can be mated with the stimulation source 16 in a standard manner.

The length of the extension lead 20 is preferably sized to extend from the mounted access anchor 12 to the implant location of the stimulation source 16. For example, if the stimulation source 16 is to be implanted in the chest region of the patient, the length of the stimulation lead 14 may be in the range of 50 cm to 100 cm. If, however, the stimulation source 16 is to be implanted in the abdomen or groin area of the patient, the length of the stimulation lead 14 may be in the range of 150 cm to 300 cm.

Referring still to FIG. 1, the implantable stimulation source 16 is designed to deliver electrical pulses to the stimulation lead 12 in accordance with programmed parameters. In the preferred embodiment, the stimulation source 16 is programmed to output electrical pulses having amplitudes varying from 0.1 to 20 volts, pulse widths varying from 0.02 to 2 milliseconds, and repetition rates varying from 2 to 2500 Hertz. In the illustrated embodiment, the stimulation source 16 takes the form of a totally self-contained generator, which once implanted, may be activated by a small magnet and/or controlled by an outside telemetry source that transmits programmed parameters to the pulse generator and monitors the performance of the pulse generator, e.g., a small magnet. In this case, the pulse generator has an internal power source that limits the life of the pulse generator to a few years, and after the power source is expended, the pulse generator must be replaced. Generally, these types of stimulation sources may be implanted within the chest or abdominal region beneath the skin of the patient.

Alternatively, the implantable stimulation source 16 may take the form of a passive receiver that receives radio frequency (RF) signals from an external transmitter worn by the patient. In this scenario, the life of the stimulation source 16 is virtually unlimited, since the stimulation signals originate from the external transmitter. Like the self-contained generators, the receivers of these types of stimulation sources can be implanted within the chest or abdominal region beneath the skin of the patient. The receivers may also be suitable for implantation behind the ear of the patient, in which case, the external transmitter may be worn on the ear of the patient in a manner similar to that of a hearing aid. Stimulation sources, such as those just described, are commercially available from Medtronic, Inc., located in Minneapolis, Minn. Further details regarding the construction of a stimulation source for the purpose of treating neurological disorders is disclosed in U.S. Pat. No. 5,716,377, which is expressly incorporated herein by reference.

The stimulation source 16 may be connected to the stimulation lead 14 or multiple stimulation leads in any one of a variety of manners. For example, each stimulation lead 14 can be connected in a unipolar arrangement or a bipolar or multipolar arrangement or multiple stimulation leads can be connected together in a bipolar arrangement, further details of which are described in U.S. Patent Application Publication 2005/0137646 A1, previously abandoned, which has previously been incorporated herein by reference.

Having described the construction and function of the cortical brain tissue stimulation kit 10, a preferred method of installing it in the patient's head to treat a diagnosed disorder via cortical brain tissue stimulation will now be described with reference to FIGS. 15A-15J. During this procedure, a standard imaging system, such as Computed Tomography (CT), Computed Tomography Angiography (CTA) or Digital Angiography can be used to facilitate installation of the kit 10.

Figure 15A:
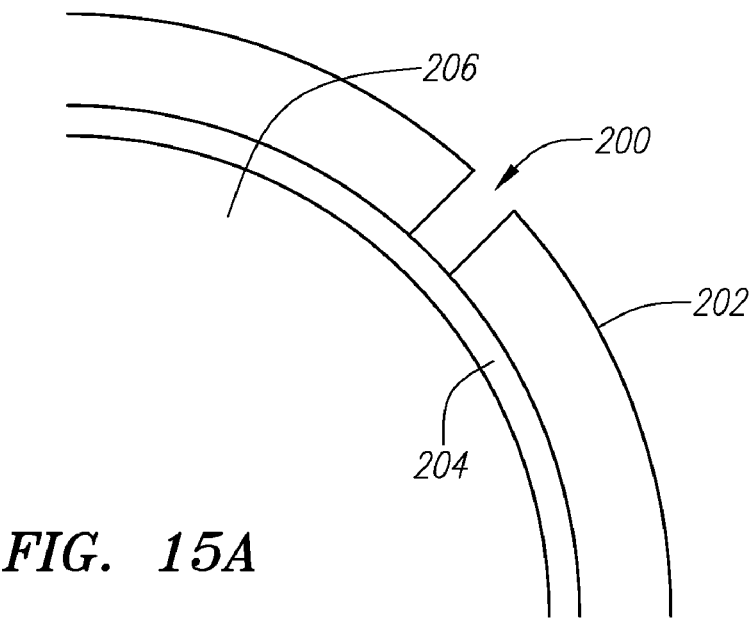
FIGS. 15A-15J illustrates a method for installing a stimulation lead within a patient using the kit of FIG. 1.
Figure 15B:
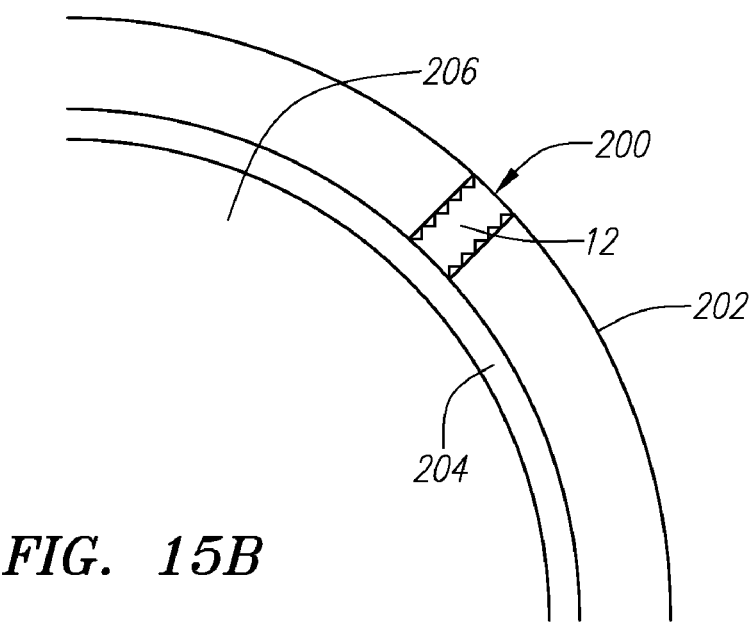

First, a relative small burr hole 200 (e.g., 2-3 millimeter diameter) is drilled through the patient's cranium 202 to access the underlying dura mater 204 that protects the cortical brain tissue 206 (FIG. 15A). Next, the access anchor 12 is installed within the burr hole 200 by inserting the distal end of the access anchor 12 into the burr hole 200 and rotating the access anchor 12 the access anchor 12 until it is flush with the external surface of the cranium 202 (FIG. 15B). The driven mechanism 32 can be engaged with an allen wrench (not shown) to rotate the access anchor 12. As previously described above, the recessed driven mechanism 32 will avoid any protrusion of the access anchor 12 from the cranium 202.

Figure 15C:
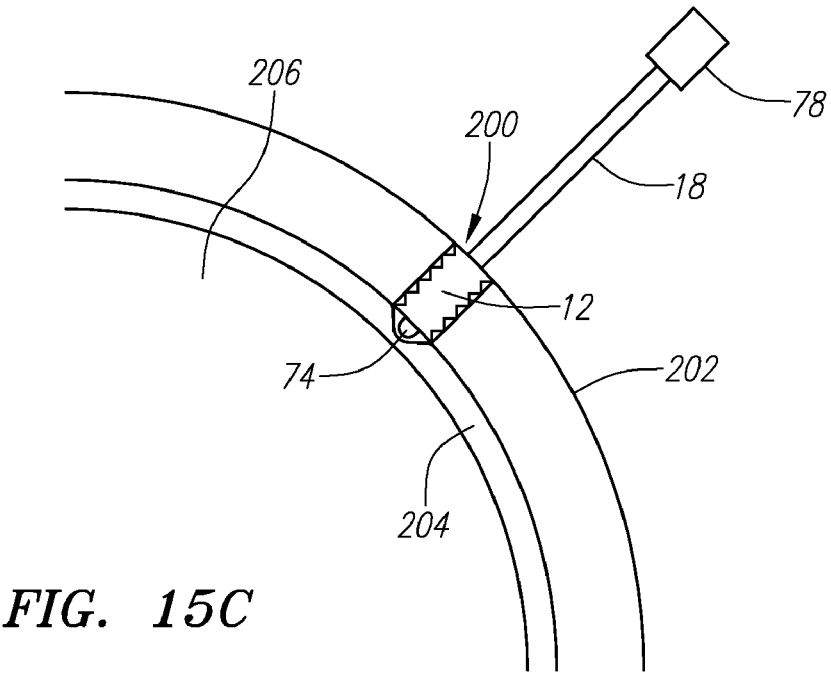
Figure 15D:
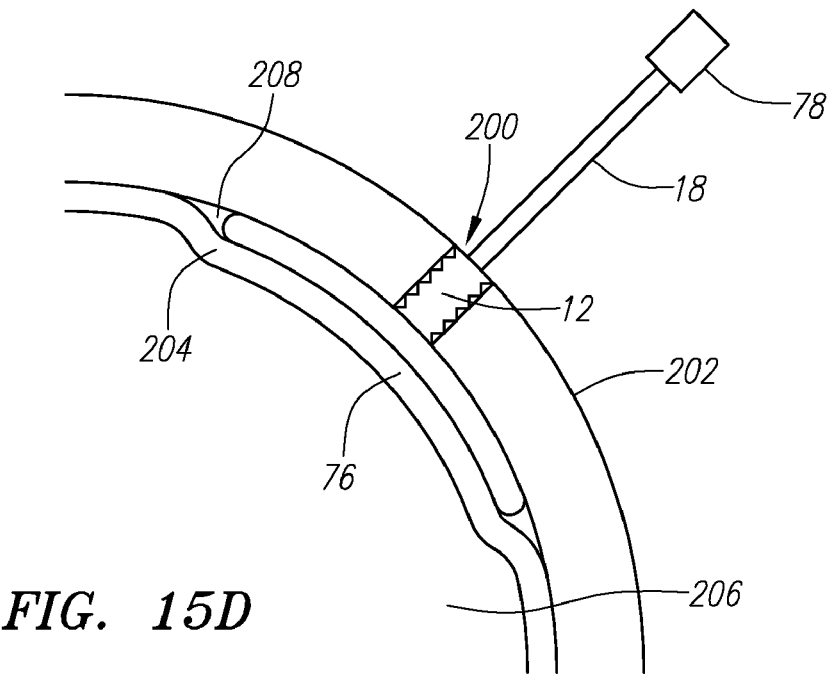

If is discovered that the dura mater 204 is adhered to the inner surface of the cranium 202, which often occurs in elderly patients, it is preferable that the tissue layer dissection device 18 be used to separate the dura mater 204 from the cranium 202. In this case, the tissue layer dissection device 18, while the balloon 76 is in its deflated geometry, is introduced through the port 28 of the access anchor 12 until the distal end 74 of the dissection device 18 contacts the dura mater 204 (FIG. 15C). Then, inflation medium is introduced through the inflation port 78 of the dissection device 18, thereby inflating the balloon 76, which will expand radially outward in a planar geometry to separate the dura mater 204 from the cranium 202 to create a pocket 208 therebetween (FIG. 15D). If the dissection device 18 has an optional monitoring lumen, any CSF or blood leakage can be detected simply by checking to see if CSF or blood is aspirated through the monitoring lumen or by placing a scope through the monitoring lumen and internally visualizing any fluid leakage. The balloon 76 is then deflated by removing the inflation medium from the inflation port 78 of the dissection device 18, which is then removed from the patient's head via the access anchor 12.

Figures 1, 15E:
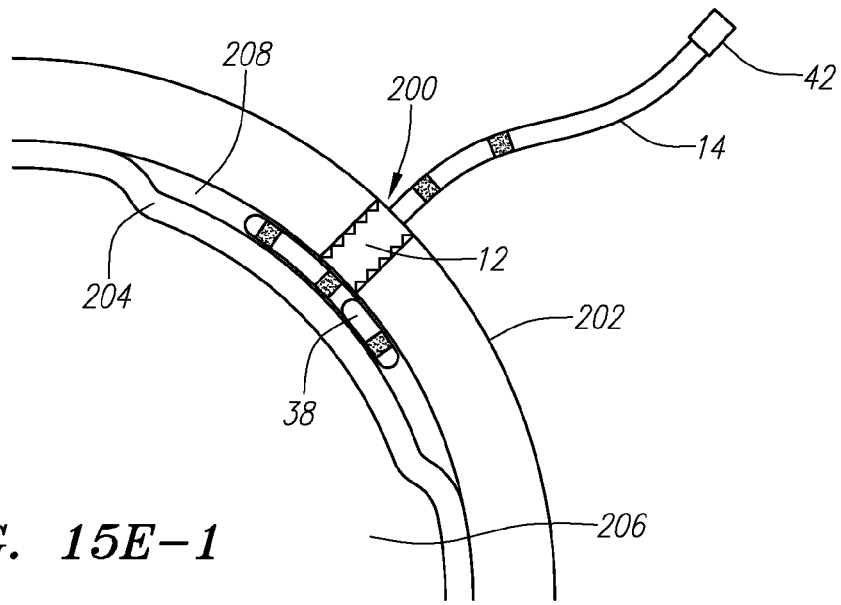
Figures 2, 15E:
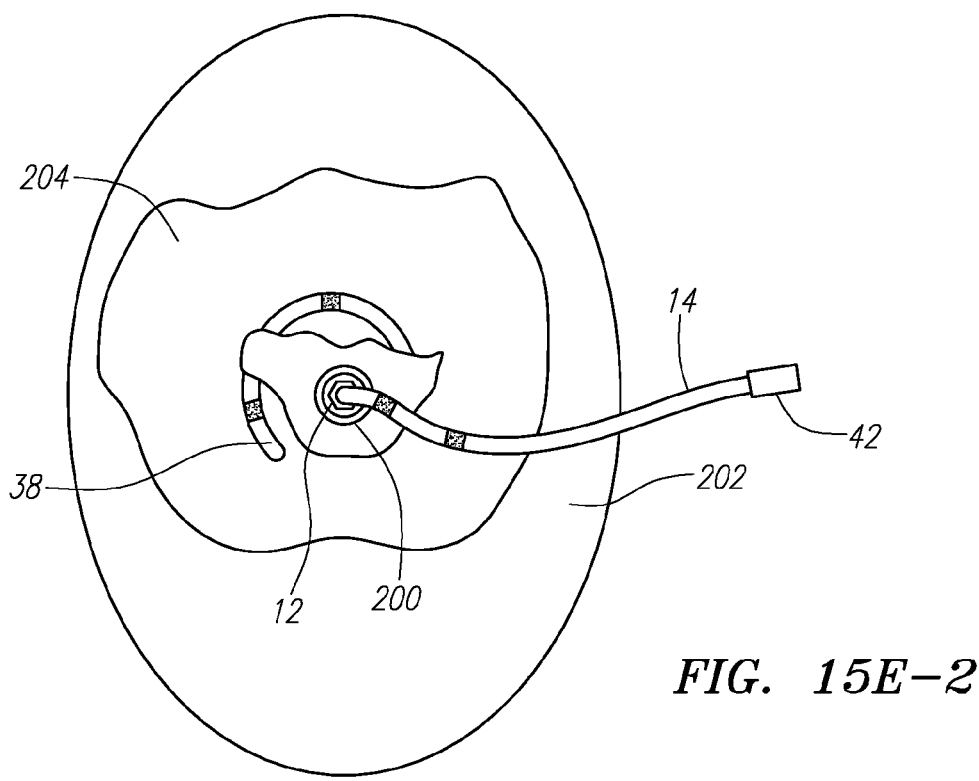
Figures 1, 15F:
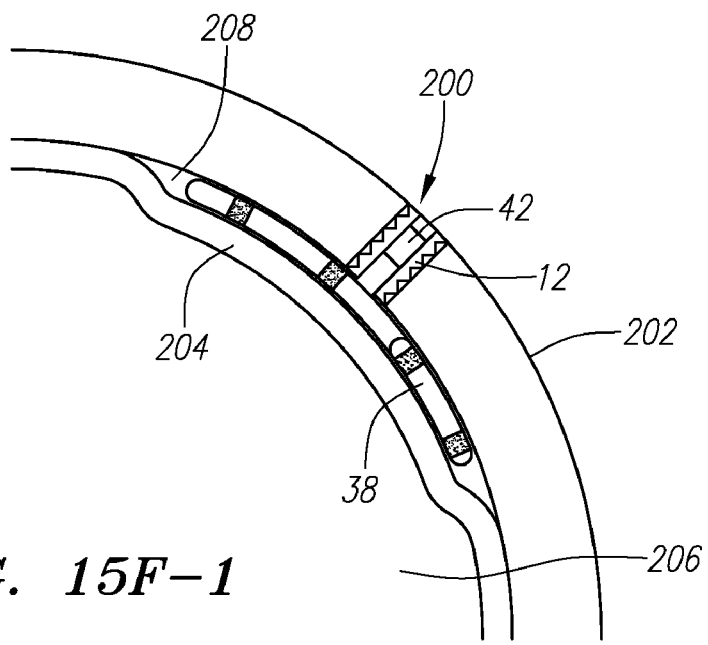
Figures 2, 15F:
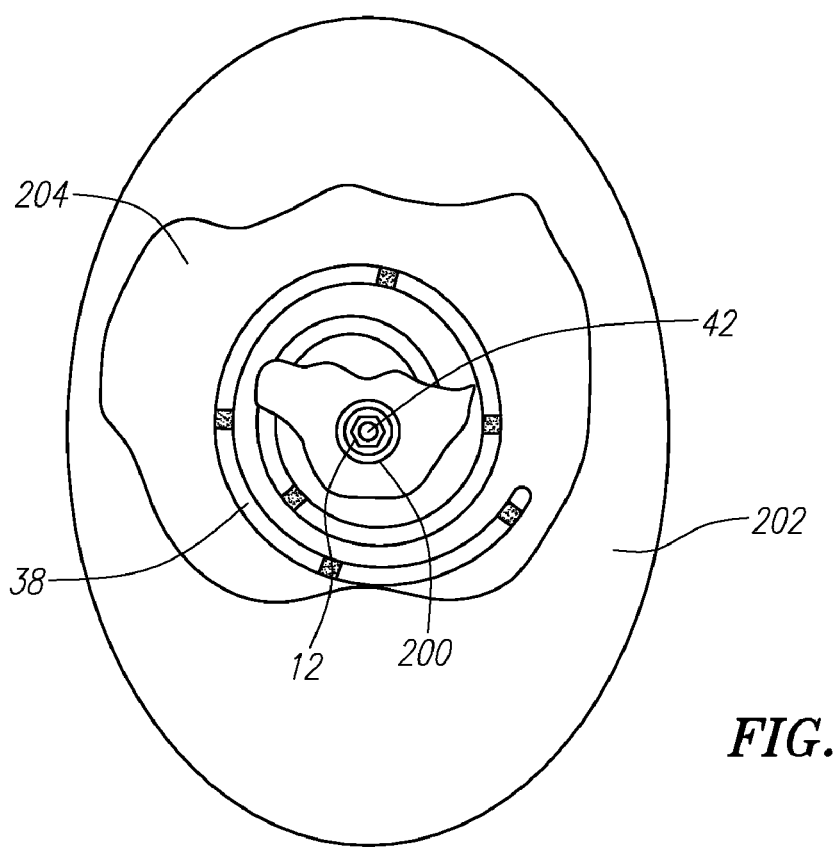

Next, a stimulation lead is introduced through the port 28 of the access anchor 12 into the pocket, where it is placed in its expanded geometry between the dura mater 204 and cranium 202. The details of this step will ultimately depend on the type of stimulation lead used. For example, if the pushable stimulation lead 14 illustrated in FIG. 6 (or alternatively, the pushable stimulation leads 54, 54 illustrated in FIGS. 7 and 8) is used, the stimulation lead 14 will be linearly introduced (i.e., by threading) through the port 28 of the access anchor 12 (FIG. 15E-1). Advancement of the stimulation lead 14 will automatically cause the distal end 38 of the stimulation lead 14 to expand by outwardly winding (FIG. 15E-2). The stimulation lead 14 will continue to be advanced through the access anchor 12 until the connector 42 of the stimulation lead 14 mates within the port 28 of the access anchor 12 (FIG. 15F-1) (see FIG. 4A for details), during which the distal end 38 of the stimulation lead 14 will be fully expanded between the dura mater 204 and cranium 202 (FIG. 15F-2).

Figure 15G:
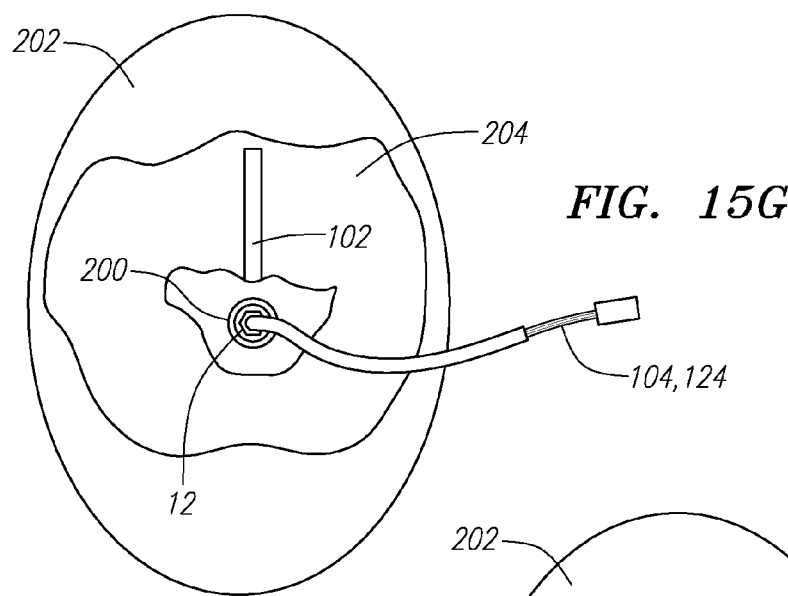
Figures 1, 15H:
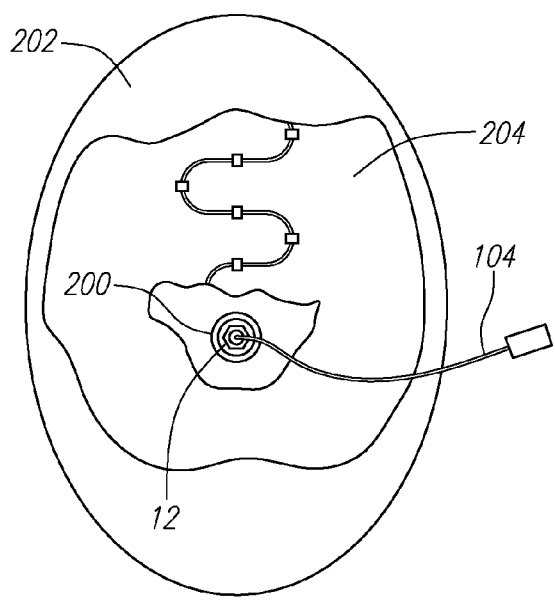
Figures 2, 15H:
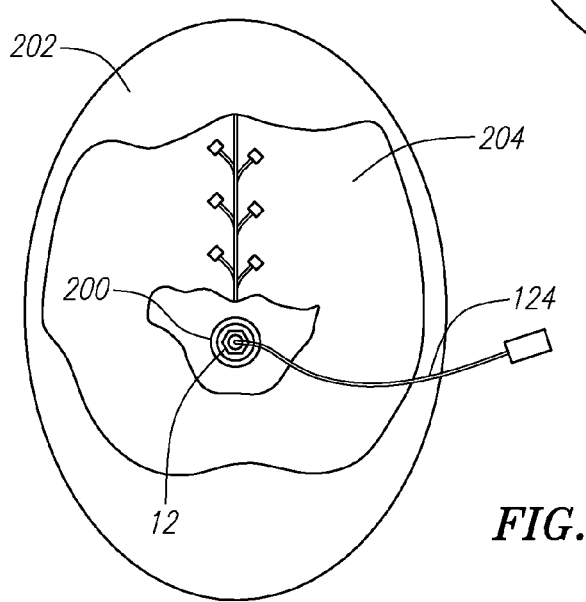
Figure 15I:
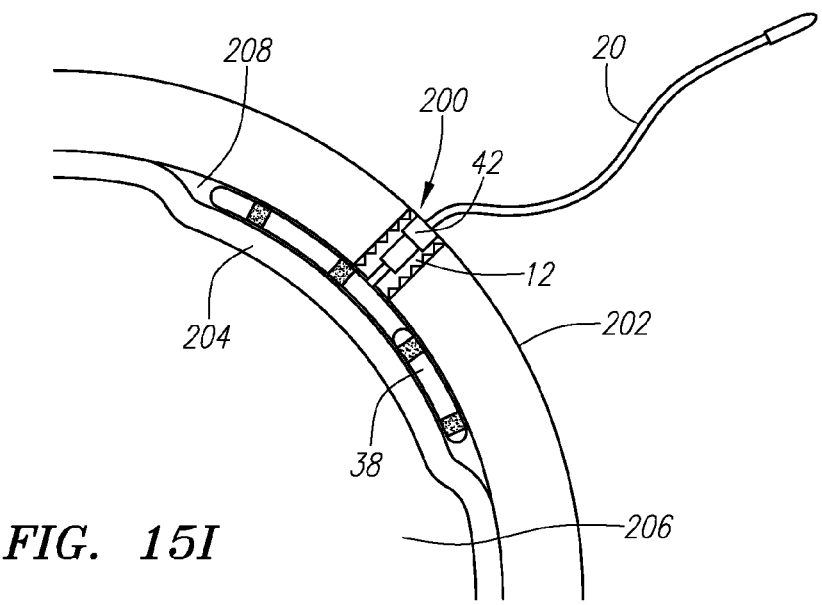

If the sheath-type stimulation leads 104, 124 illustrated in FIGS. 12 and 14 are used, the sheath 102, along with the collapsed stimulation lead 104, 124 will be threaded through the port 28 of the access anchor 12 and into the pocket 208 formed between the dura mater 204 and cranium 202 until the distal tip of the sheath 102 lies at the distal-most portion of the pocket 208 (FIG. 15G). The sheath 102 will then be pulled back and removed to expose the distal ends of the stimulation leads 104, 124, which will then fully expand between the dura mater 204 and cranium 202 (FIGS. 15H-1 and 15H-2). The stimulation lead 104, 124 will be further advanced through the access anchor 12 until the connector 42 of the stimulation lead 104, 124 mates within the port 28 of the access anchor 12 in the same manner illustrated in FIGS. 15F-1 and 15F-2.

Figure 15J:
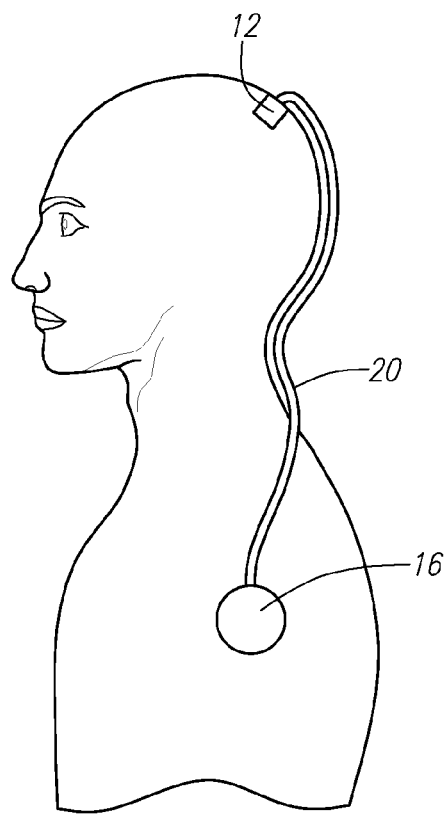

Depending on the nature of the neurological disorder and goals of the operation, the stimulation lead 14 (or leads 54, 64, 104, or 124) may be left within the patient's head either acutely (i.e., only during an operation and then removed after the operation has been completed), chronically, or sub-chronically (i.e., less than six months). After the stimulation lead 14 (or alternatively, the stimulation leads 54, 64, 104, 124) has been deployed between the dura mater 204 and cranium 202, the distal connector 42 of the extension lead 20 (which as described above takes the form of a male hexagonal connector) is snap fit into the hexagonal recess 32 of the access anchor 12 and mated with the connector 42 of the stimulation lead 14 (FIG. 15I) (see FIG. 4A for details). The extension lead 20 can then be subcutaneously routed to the clavical or chest region or the abdominal or groin region of the patient, where it can be coupled to the implanted stimulation source 16 (FIG. 15J). Alternatively, the stimulation source 16 may not be implanted, but rather located exterior to the patient. e.g., during a non-chronic procedure.

Although the stimulation kit 10 is designed to minimize the number of burr holes made within the patient's cranium, the steps illustrated in FIGS. 15A-15F and 151-15J (if pushable stimulation leads are used) and FIGS. 15A-15D and 15G-15J (if sheathed stimulation leads are used) can be repeated if additional stimulation leads are to be placed within the pocket 208 between the dura mater 204 and cranium 202. The stimulation source 16 can then be operated to transmit stimulation energy to the stimulation lead 14 (or stimulation leads 54, 64, 104, or 124), which delivers the stimulation energy to the cortical brain tissue 206 through the dura mater 204.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of delivering an electrode lead into the head of a patient, comprising:
   forming a burr hole within the cranium of the patient;
   linearly introducing the electrode lead through the burr hole;
   advancing the electrode lead between the cranium and cortical brain tissue of the patient; and
   winding the electrode lead into a two-dimensional coiled shape as the electrode lead is linearly advanced between the cranium and cortical brain tissue.

2. The method of claim 1, wherein the electrode lead is an electrical stimulation lead.

3. The method of claim 2, further comprising electrically coupling the stimulation lead to an electrical stimulation source.

4. The method of claim 2, wherein the patient suffers from a disorder, the method further comprising conveying stimulation energy from the stimulation lead to the cortical brain tissue to treat the disorder.

5. The method of claim 1, wherein the burr hole has a diameter that is equal to or less than 3 millimeters.

6. The method of claim 1, wherein the electrode lead comprises a flexible tubular body and a resilient center support extending through the flexible tubular body, thereby providing the flexible tubular body with axial rigidity and urging the electrode lead into the two-dimensional coiled shape.

7. The method of claim 1, wherein the electrode lead has a lumen and a stylet disposed within the lumen, and the stylet urges the electrode lead into the two-dimensional coiled shape from within a portion of the lumen in which the stylet is present, the method further comprising removing the stylet from the lumen after the electrode lead has been placed into the two-dimensional coiled shape between the cranium and the cortical brain tissue.

8. The method of claim 1, further comprising mounting an access anchor into the burr hole, wherein the electrode lead is introduced through the access anchor.

9. The method of claim 8, further comprising electrically coupling an extension lead to the electrode lead via the access anchor.

10. The method of claim 1, wherein the electrode lead is placed between the cranium and the dura mater of the patient.

11. The method of claim 10, further comprising:
    introducing a tissue layer dissection device through the burr hole prior to introduction of the electrode lead;
    operating the dissection device to separate the dura mater overlying the cortical brain tissue from the cranium; and
    removing the dissection device from the burr hole.

12. The method of claim 11, wherein the tissue layer dissection device comprises a balloon, and operation of the dissection device comprises inflating a balloon to separate the dura mater from the cranium, the method further comprising deflating the balloon prior to removing the dissection device from the burr hole.

13. The method of claim 1, wherein the electrode lead has a monitoring lumen, the method further comprising aspirating any fluid between the cranium and the cortical brain tissue through the lumen.

14. The method of claim 1, wherein the electrode lead has a monitoring lumen, the method further comprising introducing a scope through the lumen into the patient's head.

15. The method of claim 1, wherein the electrode lead carries a plurality of electrodes, and wherein the electrodes are arranged in the two-dimensional coiled shape.

16. The method of claim 1, wherein the electrode lead is placed in the two-dimensional coil shape along a plane conforming to a surface of the cortical brain tissue.

17. The method of claim 15, wherein the electrodes are ring electrodes.

18. The method of claim 1, wherein the electrode lead is pre-shaped with the two-dimensional coil shape.

19. The method of claim 1, wherein the electrode lead winds outwardly into the two-dimensional coil shape.

20. A method of delivering an electrode lead into the head of a patient, comprising:
    forming a burr hole within the cranium of the patient;
    linearly introducing the electrode lead through the burr hole with a sheath;
    advancing the electrode lead between the cranium and cortical brain tissue of the patient; and
    outwardly winding the electrode lead into a two-dimensional coiled shape between the cranium and cortical brain tissue as the electrode lead is axially advanced from the sheath.

21. The method of claim 1, wherein the electrode lead is introduced through the burr hole along an axis, and the two-dimensional coiled shape is formed on a plane substantially perpendicular to the axis.

* * * * *